United States Patent
Kitagawa et al.

(10) Patent No.: US 9,532,791 B2
(45) Date of Patent: Jan. 3, 2017

(54) PUNCTURE ASSISTING TOOL AND PUNCTURE TOOL ASSEMBLY

(71) Applicant: Terumo Kabushiki Kaisha, Tokyo (JP)

(72) Inventors: Tomomi Kitagawa, Fujinomiya (JP); Yasuyuki Honma, Matsuda-machi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/572,255

(22) Filed: Dec. 16, 2014

(65) Prior Publication Data
US 2015/0100099 A1   Apr. 9, 2015

Related U.S. Application Data

(63) Continuation of application No. PCT/JP2012/073378, filed on Sep. 12, 2012.

(51) Int. Cl.
A61B 17/17 (2006.01)
A61B 17/34 (2006.01)
A61B 17/70 (2006.01)

(52) U.S. Cl.
CPC ....... *A61B 17/1757* (2013.01); *A61B 17/3403* (2013.01); *A61B 17/7065* (2013.01); *A61B 2017/3407* (2013.01); *A61B 2017/3409* (2013.01)

(58) Field of Classification Search
CPC ............ A61B 17/1757; A61B 17/3403; A61B 17/7065; A61B 2017/3407; A61B 2017/3409
USPC ........ 606/246–249, 279, 86 A, 86 R, 96, 99; 623/17.11; 604/170.03
See application file for complete search history.

(56) References Cited

U.S. PATENT DOCUMENTS

| | | | |
|---|---|---|---|
| 6,530,929 B1 * | 3/2003 | Justis | A61B 17/1671 606/103 |
| 2006/0149278 A1 * | 7/2006 | Abdou | A61B 17/7077 606/90 |
| 2007/0167970 A1 | 7/2007 | Sonoda et al. | |
| 2007/0233076 A1 | 10/2007 | Trieu | |
| 2008/0306481 A1 | 12/2008 | Farr et al. | |
| 2011/0093013 A1 | 4/2011 | Perez-Cruet et al. | |

(Continued)

FOREIGN PATENT DOCUMENTS

JP   2009-532110 A   9/2009
JP   2010-508911 A   3/2010

OTHER PUBLICATIONS

International Search Report dated Oct. 16, 2012 issued in Application No. PCT/JP2012/073378.

*Primary Examiner* — Pedro Philogene
*Assistant Examiner* — David C Comstock
(74) *Attorney, Agent, or Firm* — Foley & Lardner LLP

(57) ABSTRACT

A puncture assisting tool for assisting in a puncturing operation by a puncture tool that is used to insert and place a spacer between bones and includes an arc-shaped needle includes a base section configured to be in contact with a skin of a patient; and a guide unit configured to be fixed with respect to the base section. The guide unit has a curvature that is approximately the same as a curvature of an arc shape of the puncture tool. The guide unit is configured such that an outer arc-shaped surface of the puncture tool can be placed in contact with the guide unit to guide the puncture tool in an arc trajectory while the puncture tool is being inserted into the patient.

20 Claims, 16 Drawing Sheets

(56) References Cited

U.S. PATENT DOCUMENTS

2012/0116517 A1* 5/2012 Petit ............... A61F 2/4611
623/17.16

* cited by examiner

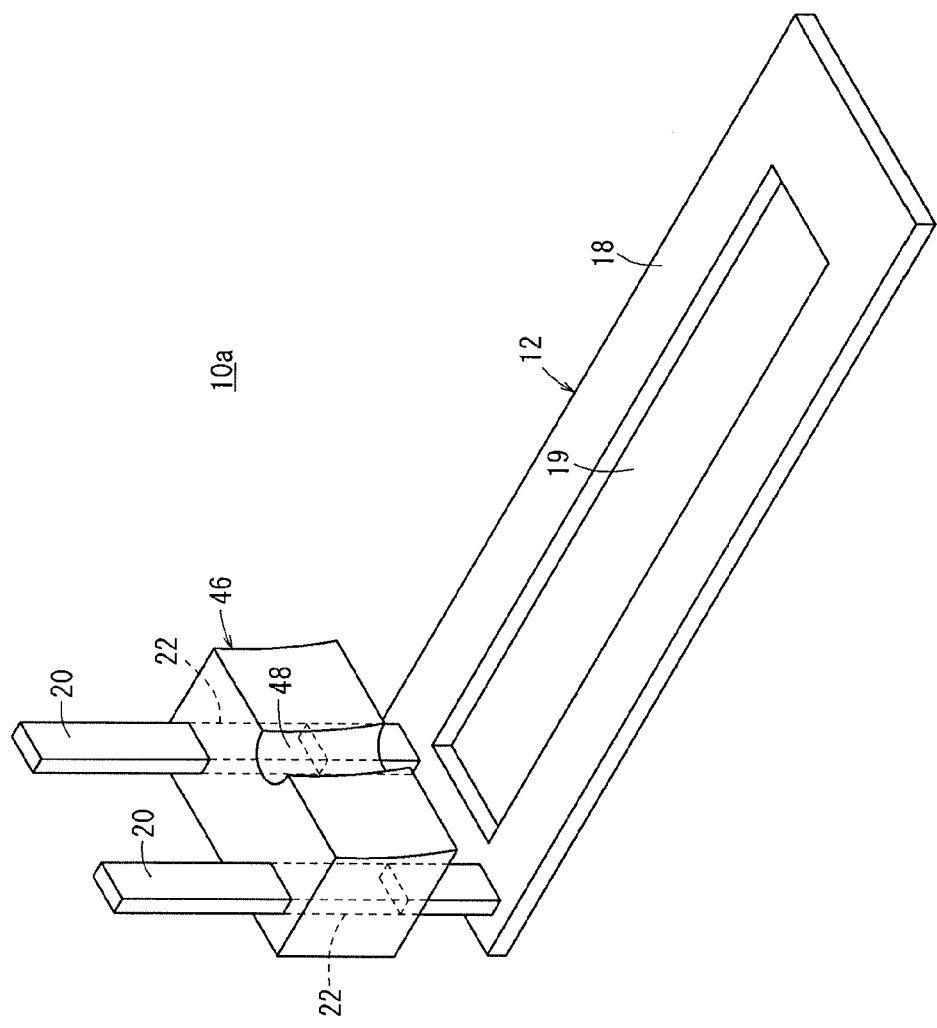

FIG. 14A
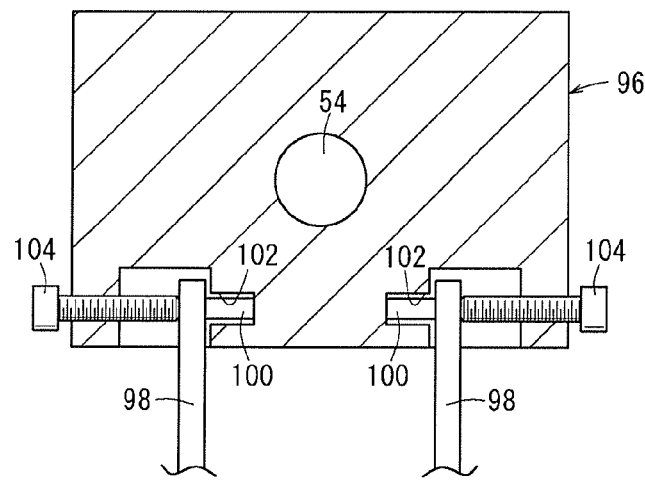
FIG. 14B
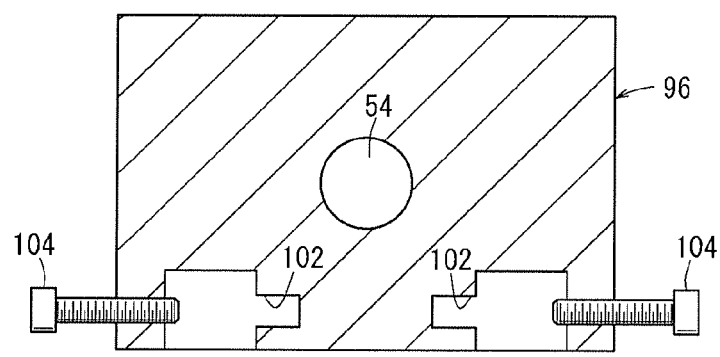
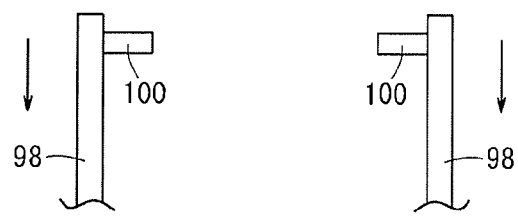

PUNCTURE ASSISTING TOOL AND PUNCTURE TOOL ASSEMBLY

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2012/073378 filed on Sep. 12, 2012, the entire contents of which is hereby incorporated by reference in its entirety.

BACKGROUND

Technical Field

The present disclosure relates to a puncture tool assembly and a puncture assisting tool that assists in a puncturing of a puncture tool which is used to insert a spacer to be placed between bones.

Background Art

Lumbar spinal canal stenosis is a stenosis of a vertebral canal caused by a regressive degeneration of an intervertebral disk, a ligament, and the like, and causes symptoms such as lumbago, melosalgia, and intermittent claudication. In order to treat the lumbar spinal canal stenosis, a surgical operation through which a spinal column of a part that narrows the vertebral canal is partially incised (laminectomy) and a surgical operation through which the spinal column is fixed (spinal fusion) are in prevalent use. In recent years, a method of placing a metallic spacer between spinous processes and releasing compression of a spinal nerve and a nerve root was developed as a relatively more minimally invasive procedure than laminectomy and a spinal fusion. However, according to the method, a back muscle and ligament have to be incised in order to place the spacer, and thus the degree of an invasion to a patient is still high, and long-term hospitalization is caused.

In order to deal with the problem, a method for inserting and placing the spacer between the spinous processes in a further minimally invasive manner has been proposed. According to this method, an expandable balloon is used as the spacer. The balloon, in a folded state, is percutaneously inserted and placed between the spinous processes. Then, the balloon is filled with a filling material such as a bone cement so that the balloon is expanded,. The filling material is cured after the balloon is filled therewith, and thus the expansion state of the balloon can be maintained semi-permanently.

US Patent Application Publication 2011/0093013A1 discloses a device for inserting and placing a hard spacer between the spinous processes. The device includes an arc-shaped needle, and the arc-shaped needle is inserted into the skin and muscle of the patient so that the spacer, which is attached to a distal end of the needle, is inserted between the spinous processes. However, because the needle is arc-shaped, a force added on a proximal end side of the needle is not transmitted to the distal end of the needle, and it is difficult to insert the needle due to a deformation of the skin and a repulsive force from the skin.

SUMMARY OF THE INVENTION

One objective of certain embodiments of the present invention is to provide a puncture assisting tool and a puncture needle assembly with which the insertion of the arc-shaped needle into the patient can be easily and accurately performed.

According to one embodiment, there is provided a puncture assisting tool that assists in a puncturing of a puncture tool, which is used to insert and place a spacer between bones and includes an arc-shaped needle. The puncture assisting tool includes a base section that is in contact with a skin of a patient, and a guide unit whose position with respect to the base section can be fixed, whose curvature is approximately the same as a curvature of the arc shape of the needle, and which is in contact with an outer side of the arc shape of the needle so that the needle is guided to be moved while drawing an arc trajectory.

According to the above-described configuration, the needle is inserted while being in contact with the guide unit when the needle is inserted into the patient, and thus a direction of force added from a proximal end side of the needle is corrected to a needle tip direction. In this manner, the force added to the needle is appropriately transmitted in a moving direction of the needle, and thus the insertion of the needle into the patient can be easily and accurately performed.

In one aspect, the puncture assisting tool may further include a guide body whose height is variable with respect to the base section, and the guide unit may be disposed in the guide body.

According to the above-described configuration, the height of the guide body is variable, and thus an insertion depth can be easily adjusted to correspond to the patient, and there is no need to prepare a puncture assisting tool that is set for each insertion depth.

In one aspect, the guide body may be steplessly adjusted in height with respect to the base section.

According to the above-described configuration, the insertion depth can be appropriately adjusted and the spacer can be inserted and placed at an accurate position between the bones.

In one aspect, the guide unit may be a hole that has approximately the same diameter as an outer diameter of the outer needle.

According to the above-described configuration, the puncture tool can be accurately and stably guided so that the puncture tool is moved while drawing the arc trajectory.

In one aspect, the guide unit may be formed into a concave shape extending in an arc shape to be in contact only with an outer side of the outer needle.

According to the above-described configuration, the configuration of the guide unit can be simplified.

In one embodiment, a puncture tool assembly includes a hollow and arc-shaped outer needle, a puncture tool that can be inserted into the outer needle and includes an inner needle which has the same curvature as the outer needle and is formed into an arc shape, a base section that is in contact with a skin of a patient, a guide unit whose position with respect to the base section can be fixed, whose curvature is approximately the same as a curvature of the arc shape of the puncture tool, and which is in contact with an outer side of the arc shape of the outer needle so that the outer needle is guided to be moved while drawing an arc trajectory, and connection device to which the puncture tool is fixed, and which is rotatably supported by the base section by using a center of curvature of the arc shape of the puncture tool as a rotation fulcrum.

According to the above-described configuration, the connection device to which the puncture tool is fixed is rotatable by using the center of curvature of the arc shape of the puncture tool as the rotation fulcrum. Accordingly, when the puncture tool is inserted into the patient, the puncture tool is guided by the guide unit and is moved while drawing an accurate arc trajectory. Accordingly, the insertion of the puncture tool into the patient can be performed more smoothly.

In one aspect, the puncture tool assembly may further include a guide body whose height is variable with respect to the base section, the guide unit may be disposed in the guide body, and a height of the rotation fulcrum of the connection device may be variable with respect to the base section.

According to the above-described configuration, the height of the guide body is variable, and thus a puncturing depth can be easily adjusted to correspond to the patient, and there is no need to prepare a puncture tool assembly that is set for each puncturing depth.

In one aspect, the puncture tool assembly may further include a pressing member that is in contact with a skin of a patient to suppress a deformation of the skin and a repulsive force from the skin at an insertion point. The guide unit may be disposed in the pressing member, and a lower end of the guide unit may face a skin contact surface of the pressing member.

According to the above-described configuration, the deformation of the skin and the repulsive force from the skin can be suppressed as the pressing member is pressed against the skin of the patient when the puncture tool is inserted into the patient. Accordingly, the insertion of the puncture tool into the patient can be further easily performed.

In one aspect, a height of the rotation fulcrum of the connection device may be variable with respect to the base section, and the guide unit may be rotatable with the same center of rotation and turning radius as a center of rotation and turning radius of the puncture tool.

According to the above-described configuration, an angle of the guide unit based on the rotation fulcrum can be changed according to the height of the rotation fulcrum of the connection device. Accordingly, there is no need to prepare a plurality of the pressing members corresponding to the height of the rotation fulcrum of the connection device.

In one aspect, the puncture tool assembly may further include a pressing member that is in contact with a skin of a patient to suppress a deformation of the skin and a repulsive force from the skin at an insertion point, and a guide body whose height is variable with respect to the base section. The guide unit may be disposed in the guide body, and a height of the rotation fulcrum of the connection device may be variable with respect to the base section.

In this manner, even with the configuration in which the guide unit is disposed to be separated from the pressing member, the force added to the puncture tool while the guide unit is in operation is appropriately transmitted in a moving direction of the puncture tool, and the deformation of the skin and the repulsive force are suppressed by the pressing operation of the pressing member against the skin. Accordingly, the insertion of the puncture tool into the patient can be easily performed.

In one aspect, the puncture tool assembly may further include linking device that links the height of the rotation fulcrum of the connection device with the height of the guide body.

According to the above-described configuration, there is no need for individually adjusting the heights of the rotation fulcrum and the guide body, and convenience of use is increased.

In one aspect, the puncture tool assembly may further include a guide body whose height is variable with respect to the base section, or a pressing member that is in contact with a skin of a patient to suppress a deformation of the skin and a repulsive force from the skin at an insertion point. The guide unit may be disposed in the guide body or the pressing member, and, among the members constituting the puncture tool assembly, the outer needle and the guide body or the pressing member may be separable from the other members.

According to the above-described configuration, only the outer needle and the guide body (or the pressing member) are left so that the other members can be removed from the patient after the puncturing of the puncture tool into the patient. Accordingly, during the subsequent insertion operation of the spacer, the surrounding members pose no inconvenience and the insertion operation can be smoothly performed.

In one aspect, a portion of the pressing member that is in contact with the skin may be formed to be round.

According to the above-described configuration, the skin contact surface of the pressing member can have a large area, and an effect of the suppression of the deformation of the skin and the repulsive force from the skin can be increased.

In one aspect, the puncture tool assembly may further include a stopper that regulates an insertion length of the puncture tool.

According to the above-described configuration, the insertion length of the puncture tool can be appropriately regulated and the puncture tool can be inserted at a desired insertion length into the living body.

In one aspect, the guide unit may be formed into a concave shape extending in an arc shape to be in contact only with an outer side of the outer needle.

According to the above-described configuration, the configuration of the guide unit can be simplified.

In one aspect, the guide unit may be a hole that has approximately the same diameter as an outer diameter of the outer needle.

According to the above-described configuration, the puncture tool can be accurately and stably guided so as to be moved while drawing the arc trajectory.

In one aspect, the connection device may have a pair of arm sections that are rotatably connected to the base section and extend in parallel with each other and a connection section that connects the pair of arm sections with each other on the opposite side from the rotation fulcrum.

According to the above-described configuration, the spacer that transmits radiation from above without blocking the radiation is formed between the pair of arm sections. Accordingly, when a perspective image using the radiation is obtained, the connection device poses no inconvenience.

BRIEF DESCRIPTION OF THE DRAWINGS

FIG. 7 is an overall perspective view of a puncture assisting tool that includes a guide body according to a modification example.

FIG. 14A is a view showing a connection structure between a pressing member and an arm, and FIG. 14B is a view showing a state where the pressing member and the arm are separated from each other.

DETAILED DESCRIPTION

Hereinafter, preferred embodiments of a puncture assisting tool and a puncture tool assembly according to the present invention will be described referring to the accompanying drawings.

Embodiment of Puncture Assisting Tool 10

Figure 1:
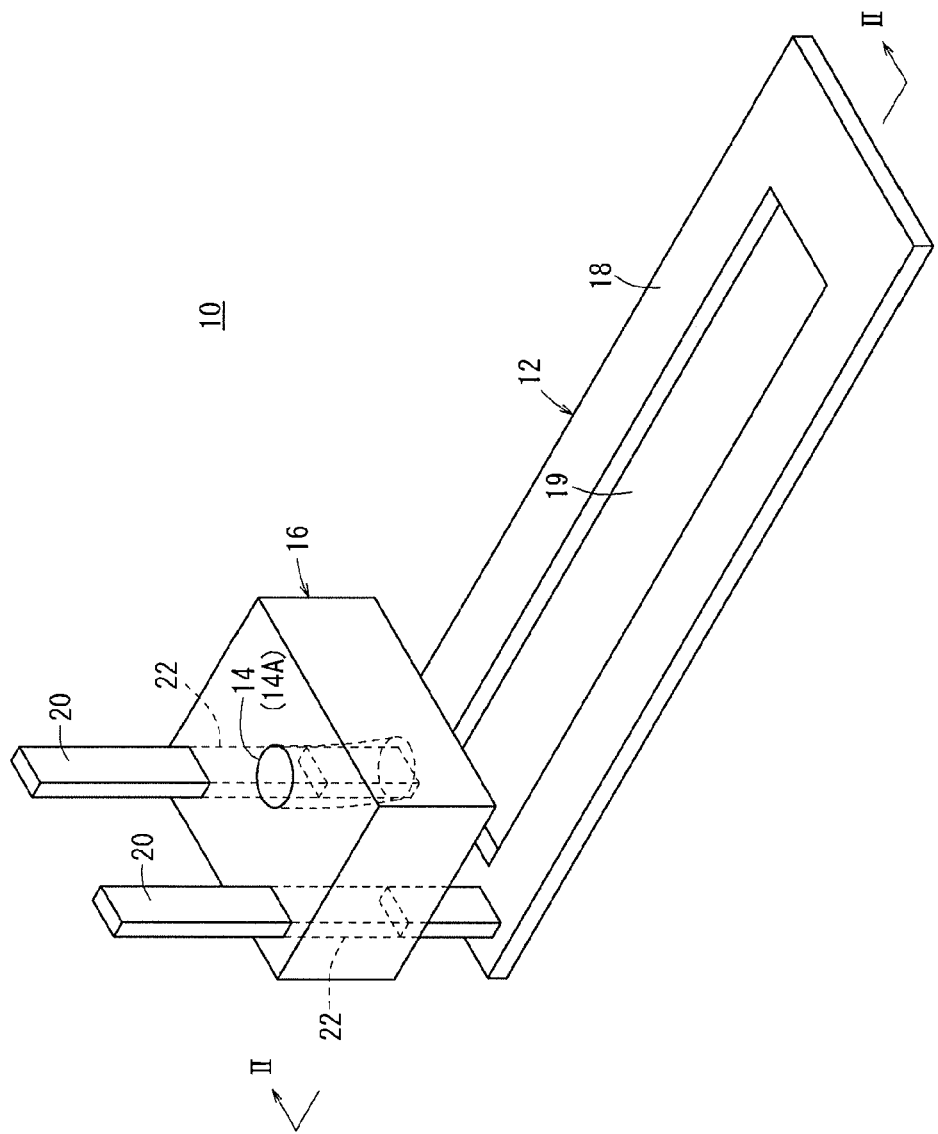
FIG. 1 is an overall perspective view of a puncture assisting tool according to an embodiment of the present invention.
Figure 2:
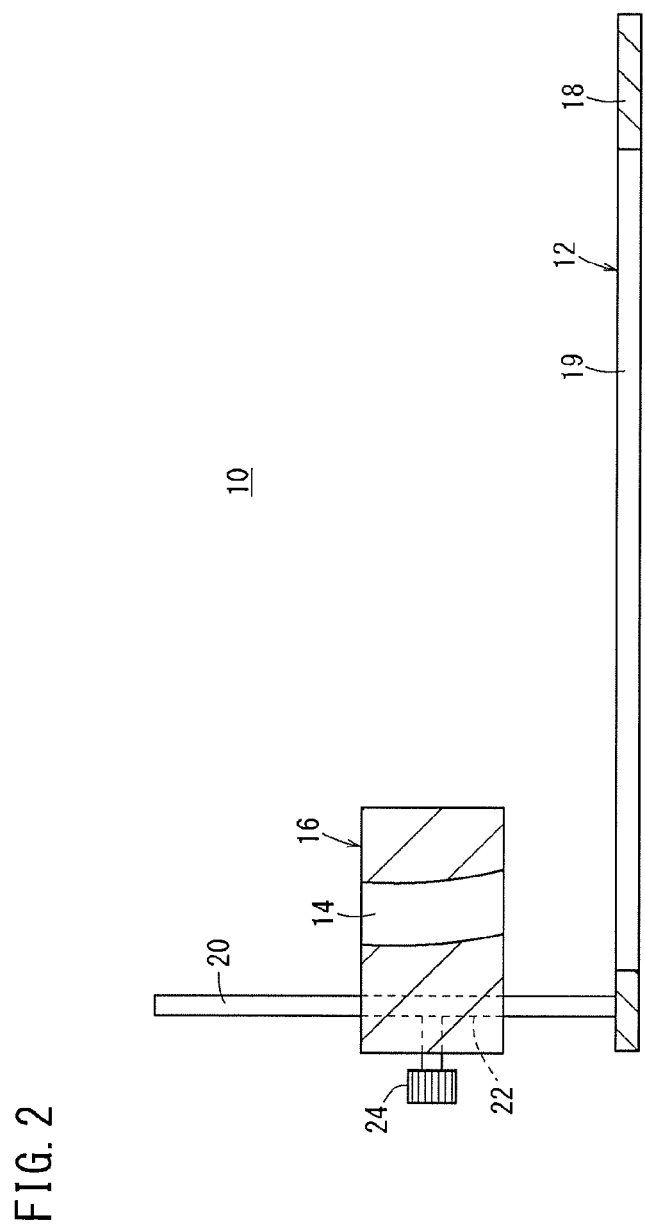
FIG. 2 is a longitudinal cross-sectional view taken along line II-II of FIG. 1.
Figure 3:
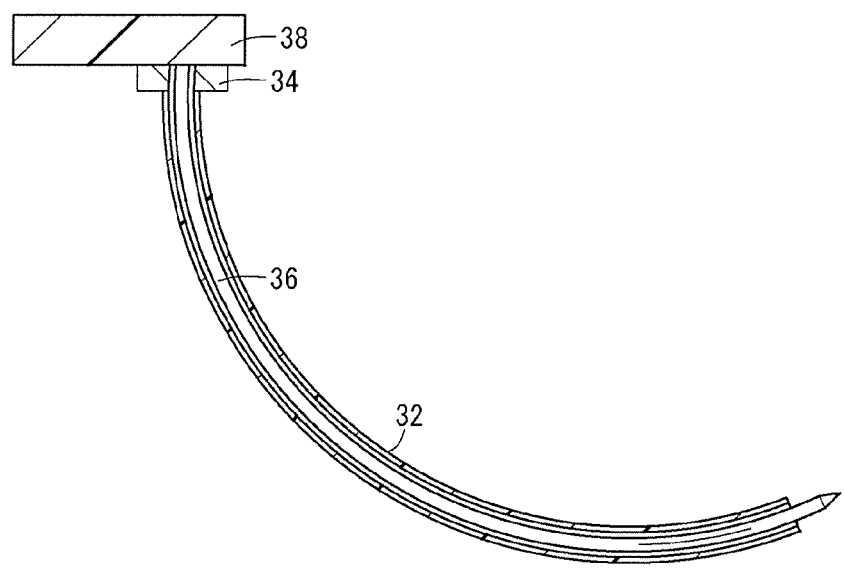
FIG. 3 is a longitudinal cross-sectional view of a puncture tool according to a configuration example that can be applied to the puncture assisting tool shown in FIG. 1.

FIG. 1 is an overall perspective view showing a configuration of the puncture assisting tool 10 according to one embodiment of the present invention. FIG. 2 is a longitudinal cross-sectional view taken along line II-II of FIG. 1. FIG. 3 is a longitudinal cross-sectional view of a puncture tool 30 according to a configuration example that can be applied to the puncture assisting tool 10. First, a configuration of the puncture tool 30 will be described referring to FIG. 3.

The puncture tool 30 is used to insert and place a spacer 42 (refer to FIG. 6A and the like) between bones. A site where the spacer 42 is inserted is, for example, between spinous processes, a shoulder joint, and an intervertebral disk. The spacer 42 that is inserted between the bones is contracted in an initial state, and is expanded when a filling material is injected.

The puncture tool 30 has a hollow and arc-shaped outer needle 32, a hub 34 that is fixed to a proximal end of the outer needle 32, an inner needle 36 that can be inserted into the outer needle 32, has the same curvature as the outer needle 32, and is formed to have an arc shape, and a handle 38 that is fixed to a proximal end of the inner needle 36. FIG. 3 shows a state where the inner needle 36 is inserted innermostly into a hollow section of the outer needle 32.

The outer needle 32, both ends of which are open, is a member that has a hollow structure which has the hollow section into which the inner needle 36 can be inserted. The hub 34 that is fixed to the proximal end of the outer needle 32 is larger in outer diameter than the outer needle 32, and is disposed in a flange shape.

The inner needle 36 is a rod-shaped member that is curved into an arc shape, which is inserted into the hollow section of the outer needle 32 and has a sharp needle tip at a distal end. A length of the inner needle 36 is set such that the distal end of the inner needle 36 projects a predetermined length from a distal end of the outer needle 32 when the inner needle 36 is fully inserted into the outer needle 32 (when the inner needle 36 is inserted into the outer needle 32 to a position where the handle 38 and the hub 34 are in contact with each other). The inner needle 36 may have a solid structure or a hollow structure. The handle 38 that is disposed at the proximal end of the inner needle 36 is a site that functions as a grip which is gripped by a user of the puncture tool 30. In FIG. 3, the handle 38 is disposed to extend radially outward from the arc shape of the inner needle 36.

Materials constituting the outer needle 32 and the inner needle 36 are not particularly limited if the material is a hard material that has a moderate strength not to be damaged or deformed during puncturing into a living body. Examples thereof include a metal such as stainless steel, an aluminum alloy, and a copper-based alloy, or a hard resin such as polyvinyl chloride and polyethylene. Materials constituting the hub 34 and the handle 38 are not particularly limited, but the hard materials exemplified above as the material of the outer needle 32 and the inner needle 36 can be adopted.

An X-ray opaque marker may be installed at least at a portion of a distal end side of the outer needle 32 or the inner needle 36 to allow recognition by X-ray fluoroscopy.

Next, the puncture assisting tool 10 will be described. As shown in FIGS. 1 and 2, the puncture assisting tool 10 includes a base section 12 that is configured to be in contact with a skin of a patient, a guide unit 14 that guides a movement of the puncture tool 30, a guide body 16 where the guide unit 14 is formed. The base section 12 has a plate-shaped contact plate 18, and guide rails 20 that project upward from one end side of the contact plate 18.

In this embodiment, the contact plate 18 is formed into a flat plate shape that is long in one direction, and a long hole-shaped hole section 19 is formed along a longitudinal direction thereof. The contact plate 18 is not limited to the flat plate shape, but may be configured into a curved shape or a wave shape to match the shape of the skin when put on the skin of the patient. A plurality of small projections may be disposed on a lower surface of the contact plate 18, and the contact plate 18 and the skin may be configured to be in point contact with each other at a plurality of positions so that the contact plate 18 is stabilized when the contact plate 18 is put on the skin of the patient. In addition, a gel-like sheet may be attached to a contact site between the contact plate 18 and the skin so as to be changed and attached according to the shape of the body and fit the shape of the body.

In this embodiment, a pair of the guide rails 20 are disposed apart from each other in a short direction of the contact plate 18, and support the guide body 16 such that a position thereof can be changed upward and downward. The guide rails 20 extend in parallel with each other and upward from one end side of the contact plate 18.

The guide unit 14 has a curvature that is approximately the same as curvatures of the arc shapes of the outer needle 32 and the inner needle 36, and is in contact with an outer side of the arc shape of the outer needle 32 such that the outer needle 32 is guided in such a manner as to be moved while drawing an arc trajectory. In this embodiment, the guide unit 14 is configured to have a hole 14A that has an inner diameter which allows the outer needle 32 to be inserted. An inner diameter of the guide unit 14 may be slightly larger than an outer diameter of the outer needle 32 or be approximately the same as the outer diameter of the outer needle 32 such that the outer needle 32 is moved while drawing an accurate arc trajectory.

The guide unit 14 is formed in the guide body 16. Specifically, the guide body 16 is a block-shaped member, and both ends of the guide unit 14 are open to an upper surface and a lower surface thereof. Two slide holes 22 are formed in an up-down direction through the guide body 16. The guide rails 20 are inserted into the slide holes 22. Accordingly, a height of the guide body 16 can be adjusted along the guide rails 20. Only one of the guide rails 20 may be disposed.

As shown in FIG. 2, a fixing screw 24 is disposed in the puncture assisting tool 10 so as to fix the position of the guide body 16 with respect to the guide rail 20. The fixing screw 24 is screwed to a side surface of the guide body 16. In a state where the fixing screw 24 is loosened, the guide body 16 can be moved with respect to the guide rail 20 because a distal end of the fixing screw 24 is apart from the guide rail 20. In a state where the fixing screw 24 is fastened and the distal end of the fixing screw 24 abuts against the guide rail 20, the movement of the guide body 16 with respect to the guide rail 20 is prevented and the height of the guide body 16 can be fixed to the position. In this manner, the fixing screw 24 functions as means for steplessly adjusting the height of the guide body 16.

The means for steplessly adjusting the height of the guide body 16 with respect to the base section 12 is not limited to the fixing screw 24, but may be those by fitting between the guide body 16 and the guide rail 20 and other physical engagement means. In addition, the means for adjusting the height of the guide body 16 with respect to the base section 12 is not limited to the means for the stepless adjustment, but may be those that can adjust the height with a small pitch.

A member constituting the puncture assisting tool 10 is not particularly limited if the member is a hard material that has a moderate strength not to be damaged or substantially deformed when the puncture tool 30 is guided such that the puncture tool 30 is punctured into the living body. Examples thereof include a metal such as stainless steel, an aluminum alloy, and a copper-based alloy, or a hard resin such as polyvinyl chloride and polyethylene.

Basically, the puncture assisting tool 10 according to this embodiment is configured as described above. Hereinafter, an operation and effect thereof will be described.

Herein, a procedure in which the spacer is percutaneously inserted and placed between adjacent spinous processes in the living body by using the above-described puncture tool 30 and the puncture assisting tool 10 will be described referring mainly to FIGS. 4A to 6B. In FIGS. 4A to 6B, reference numeral B is a vertebra, and reference numeral B1 is spinous processes that are formed in a back of a vertebra B.

Figure 4A:
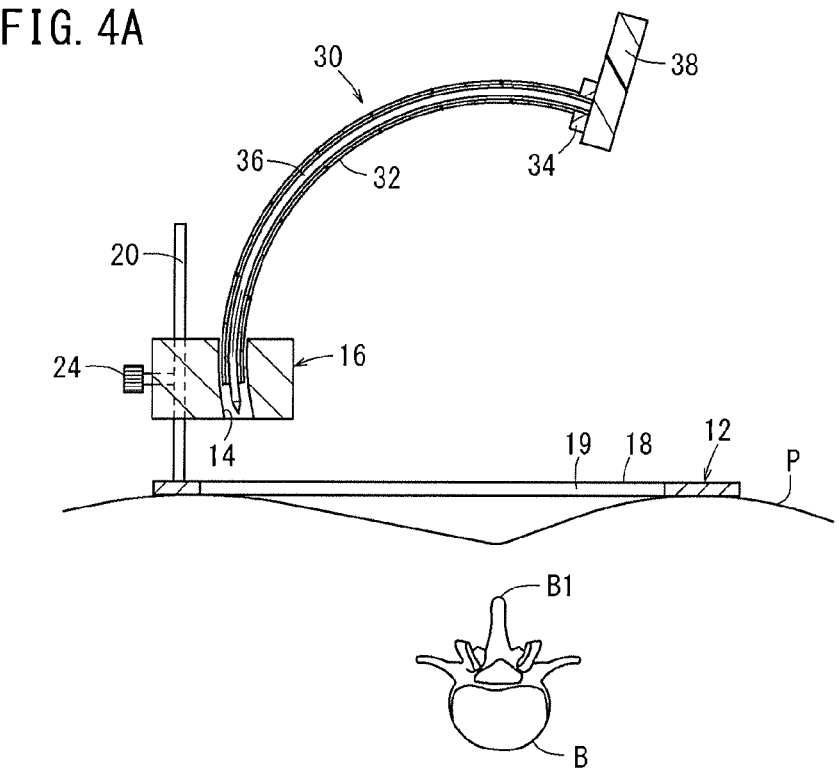
FIG. 4A is a first longitudinal cross-sectional view illustrating a method of using the puncture tool showing the puncture tool before it is inserted into the patient.

First, a patient P is put into a prone position after a lesion is determined by an X-ray fluoroscopy device, MRI, an ultrasonic diagnostic device, and the like. Next, as shown in FIG. 4A, the puncture assisting tool 10 is put on a back of the patient P in the prone position. A distance between the skin of the back of the patient P and the spinous processes to be treated is different from patient to patient, and thus the height of the guide body 16 with respect to the base section 12 is adjusted in advance. In other words, the height of the guide body 16 with respect to the base section 12 is adjusted such that a distal end side of the puncture tool 30 is inserted between the target spinous processes when the puncture tool 30 is moved along the guide unit 14 and is inserted at a predetermined length into the patient P.

Next, with the inner needle 36 being inserted into the outer needle 32, the puncture tool 30 is inserted into the guide unit 14 that is disposed in the guide body 16, and the puncture tool 30 is inserted into the patient along the guide unit 14 in X-ray fluoroscopy. In this case, the user (surgeon) of the puncture tool 30 grips the handle 38 and adds force so as to insert the puncture tool 30. Because the puncture tool 30 is inserted while being in contact with the guide unit 14, a direction of the force added from a proximal end side of the puncture tool 30 is appropriately transmitted in a moving direction (needle tip direction) of the puncture tool 30. In other words, because the curvatures of the outer needle 32 and the guide unit 14 are approximately the same as each other, the puncture tool 30 can be moved such that the arc trajectory of the same center of curvature and radius of curvature as the outer needle 32 is drawn by moving the puncture tool 30 in a distal end direction while bringing the guide unit 14 and the outer needle 32 into contact with each other.

The hole section 19 is disposed in the contact plate 18, and thus the patient P is directly irradiated with an X-ray through the hole section 19 when an insertion length (insertion depth) of the puncture tool 30 is determined by emitting the X-ray from above the puncture assisting tool 10. In other words, the hole section 19 that is disposed in the contact plate 18 is a space that passes the X-ray which is emitted from above as it is, and thus an X-ray fluoroscopic image can be appropriately obtained without the X-ray being attenuated by a structure of the puncture assisting tool 10.

Figure 4B:
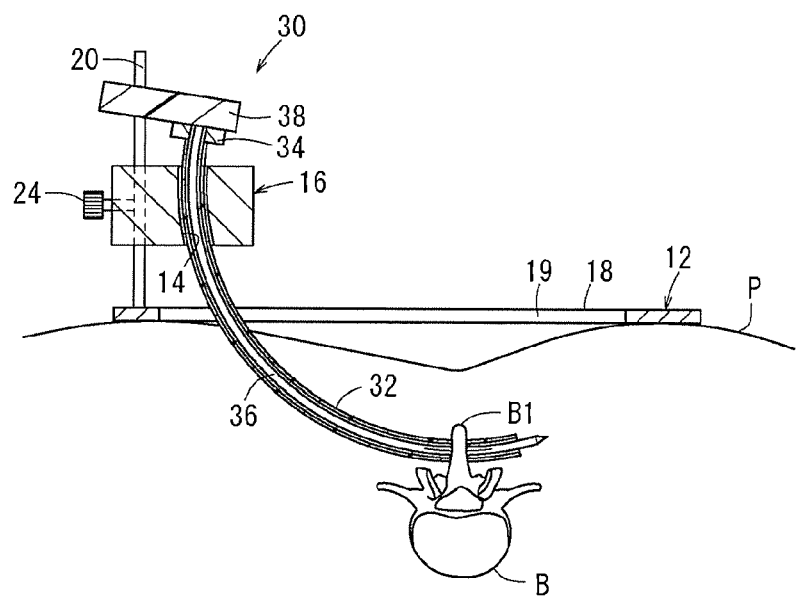
FIG. 4B is a second longitudinal cross-sectional view illustrating the method of using the puncture tool showing the puncture tool inserted into the patient.

As shown in FIG. 4B, an interspinal ligament between the adjacent spinous processes is passed in a direction crossing an axial direction of a spinal column by using the outer needle 32 and the inner needle 36 of the puncture tool 30. In this case, a distal end section of the puncture tool 30 is inserted into a position a predetermined length beyond between the spinous processes. After the puncture tool 30 is inserted at a desired length, the inner needle 36 is removed from the outer needle 32 and the outer needle 32 is placed with the position of the outer needle 32 being maintained, that is, with the outer needle 32 being inserted into the patient P.

Figure 5A:
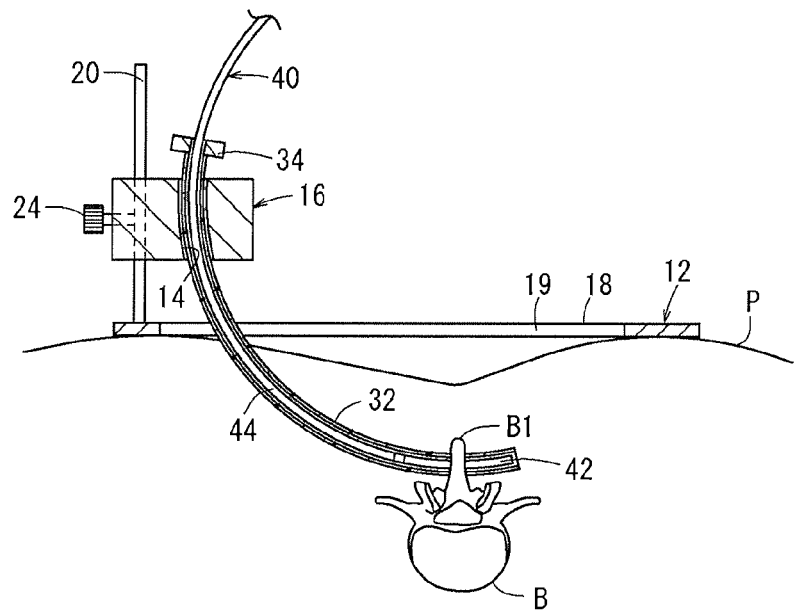
FIG. 5A is a third longitudinal cross-sectional view illustrating the method of using the puncture tool showing an expansion device inserted into the hollow section of the outer needle.

Next, as shown in FIG. 5A, an expansion device 40, which has the spacer 42 at a distal end, is inserted into the hollow section of the outer needle 32. The expansion device 40 has the expandable spacer 42, and a tube 44 that is connected to a proximal end side of the spacer 42 and has flexibility. The spacer 42 that is shown is configured as a balloon, is a tubular body when contracted, and has a structure in which a pair of bloated parts 42a are connected with each other via a constricted part 42b when expanded (refer to FIG. 6A). It is preferable that a shape of the expanded spacer 42 be a dumbbell shape, a wheel shape (H shape), or the like because the pair of bloated parts 42a which are arranged on both sides of the constricted part 42b inserted into the interspinal ligament have a form pinching the spinous processes.

A material of the spacer 42 is not particularly limited if the spacer 42 can be expanded when a filling material is injected and the material is durable to an external pressure resulting from a movement of a tissue around the spacer 42 such as the spinous processes, the interspinal ligament, and the like and a vertebral body. Examples of materials of the spacer include polyvinyl chloride, a polyurethane elastomer, nylon, and PET.

The tube 44 that is connected to the spacer 42 sends the filling material to the spacer 42, and a filling material supply source such as a syringe and a pump is connected to a proximal end side thereof. The spacer 42 and the tube 44 are connected in a separable manner. A connection structure between the spacer 42 and the tube 44 is, for example, a screwed structure. When more than a predetermined torque is applied to the spacer 42 and the tube 44, the screwing is loosened and the spacer 42 and the tube 44 are separated from each other.

As the connection structure between the spacer 42 and the tube 44, not only the above-described screwed structure but also a configuration that is releasably connected by physical engagement (fitting, hooking, and the like) and a configuration that is releasably connected when a member is decoupled through any physical operation (thermal operation, chemical operation, and the like) can be adopted.

Figure 5B:
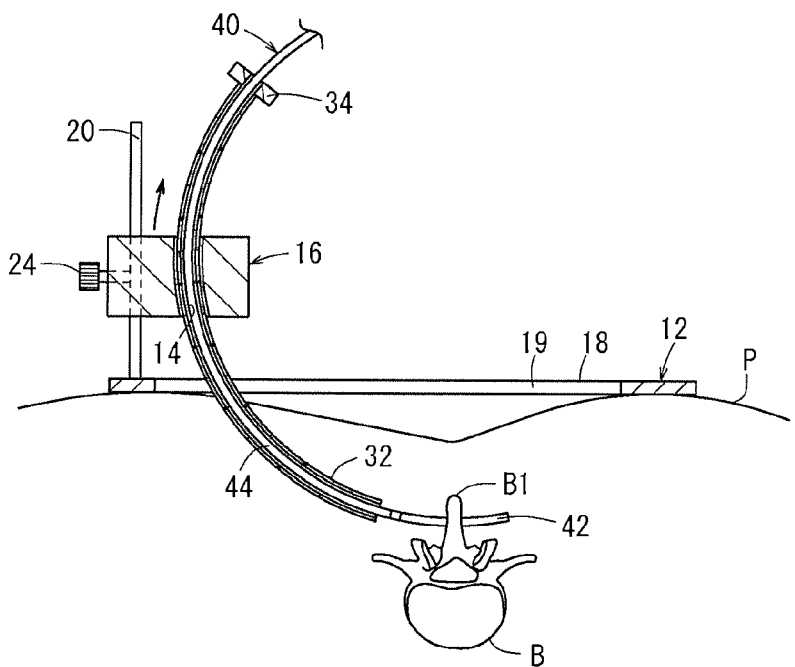
FIG. 5B is a fourth longitudinal cross-sectional view illustrating the method of using the puncture tool showing the outer needle partially withdrawn.

As shown in FIG. 5A, in a step of inserting the expansion device 40 into the hollow section of the outer needle 32, the expansion device 40 is inserted such that an axial direction center of the spacer 42 is positioned at a center of the interspinal ligament between the adjacent spinous processes. After the expansion device 40 is inserted to a predetermined position of the outer needle 32, the outer needle 32 is withdrawn in a proximal end direction with a position of the spacer 42 being maintained as shown in FIG. 5B. In this case, the outer needle 32 is withdrawn to a position where a total length of the spacer 42 is exposed to the body. When the outer needle 32 is withdrawn, the withdrawal movement of the outer needle 32 can be smoothly performed because the guide unit 14 guides the outer needle 32 such that the arc trajectory is drawn.

Figure 6A:
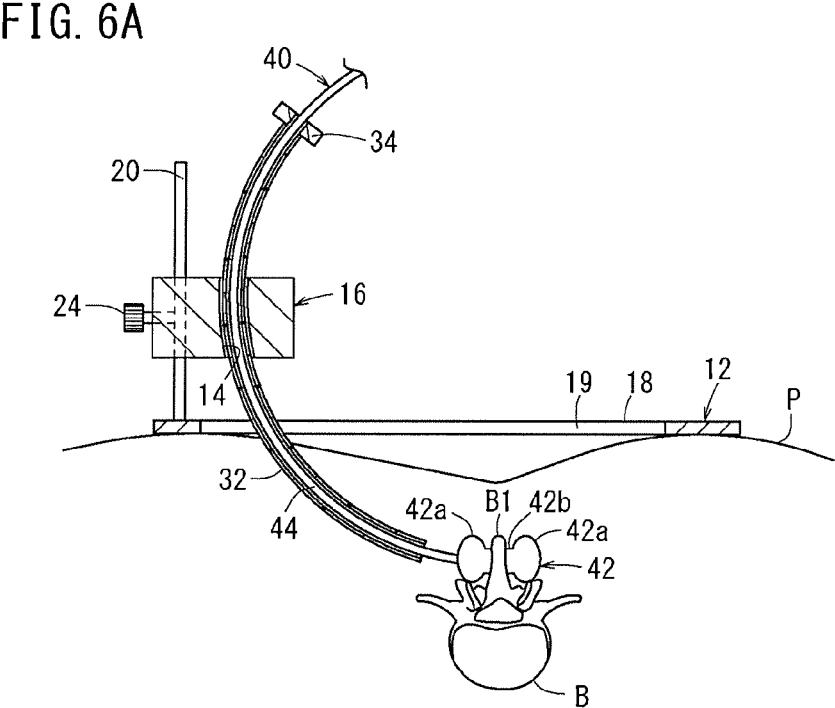
FIG. 6A is a fifth longitudinal cross-sectional view illustrating the method of using the puncture tool showing an expanded spacer at the end of a tube.

Next, as shown in FIG. 6A, the filling material supply source, which is not shown, is operated and the spacer 42 is injected with the filling material via the tube 44 such that the spacer 42 is expanded. Any material that is a fluid during the injection and is cured after the injection (for example, a bone cement, an acrylic resin, and a two-part type crosslinking polymer) or that is a fluid during the injection and even after the injection can be applied as the filling material. The expanded spacer 42 has the shape in which the pair of bloated parts 42a are connected with each other via the constricted part 42b. The constricted part 42b passes through the interspinal ligament between the spinous processes, and the interspinal ligament is positioned between the pair of bloated parts 42a on both of the sides thereof. In this manner, a gap between the spinous processes is expanded by the expanded constricted part 42b, and the spacer 42 is in a state where the spacer 42 is prevented from being removed from the interspinal ligament between the spinous processes.

Figure 6B:
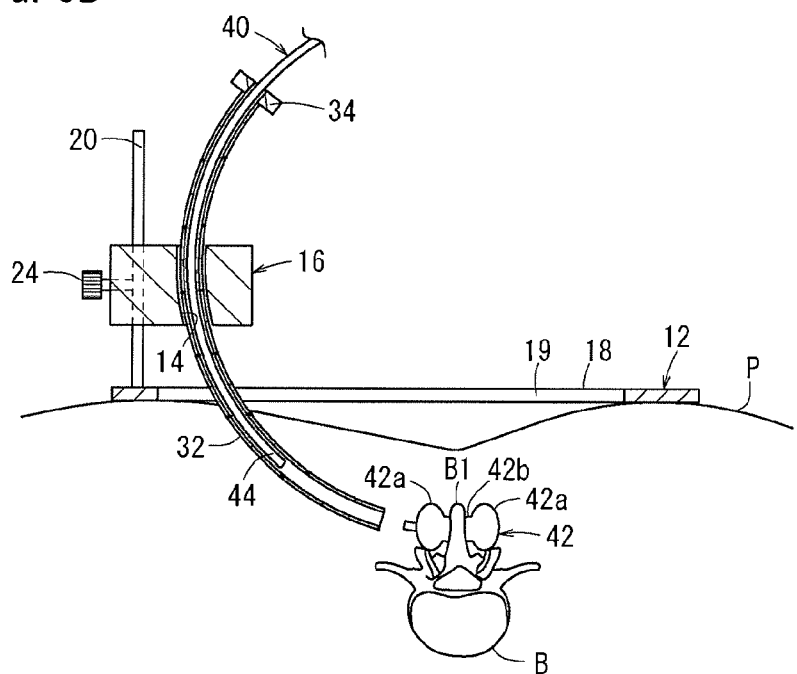
FIG. 6B is a sixth longitudinal cross-sectional view illustrating the method of using the puncture tool showing the tube released from the spacer.

After the spacer 42 is expanded, the tube 44 is released from the spacer 42 as shown in FIG. 6B. In a case where the connection structure between the spacer 42 and the tube 44 is the screwed structure, the spacer 42 that is inserted into the interspinal ligament between the adjacent spinous processes is not rotated when the tube 44 is rotated about an axis thereof, and only the tube 44 is rotated such that the screwing between the spacer 42 and the tube 44 is loosened. In this manner, the tube 44 can be released from the spacer 42.

In a case where the filling material is a material that is a fluid during the injection and is cured after the injection, the separation between the tube 44 and the spacer 42 may be performed after the curing of the filling material. In a case where the filling material is a material that is a fluid even after the injection, a backflow prevention structure (check valve) may be disposed in an inlet section of the spacer 42.

After the tube 44 is released from the spacer 42, the tube 44 is removed from the outer needle 32 and the outer needle 32 is completely removed from the patient. In this manner, the spacer 42 is in a state where the spacer 42 is placed between the spinous processes.

As described above, according to the puncture assisting tool 10 of this embodiment, the needle is inserted while being in contact with the guide unit 14 when the needle is inserted into the patient, and thus the direction of the force added from the proximal end side of the needle is corrected to the needle tip direction. In this manner, the force added to the puncture tool 30 is appropriately transmitted in the moving direction (needle tip direction) of the puncture tool 30, and thus the insertion of the needle into the patient can be easily performed. In addition, the puncture tool 30 can be accurately inserted into a target position.

In the case of this embodiment, because the height of the guide body 16 is variable, the insertion depth of the puncture tool 30 can be easily adjusted according to the shape of the body of the patient (distance between the back and the spinous processes), and there is no need to prepare the puncture assisting tool 10 that is set individually for each insertion depth.

In the case of this embodiment, the height of the guide body 16 can be steplessly adjusted with respect to the base section 12, and thus the insertion depth of the puncture tool 30 can be appropriately adjusted and the spacer 42 can be inserted and placed into an accurate position between the bones.

In the case of this embodiment, the guide unit 14 that is disposed in the guide body 16 has a form of the hole 14A whose inner diameter is approximately the same as or slightly larger than the outer diameter of the outer needle 32, and thus the outer needle 32 can be moved while drawing the accurate arc trajectory. Accordingly, insertion resistance can be further appropriately reduced when the outer needle 32 is inserted into the patient.

FIG. 7 is an overall perspective view of the puncture assisting tool 10 according to a modification example. In the puncture assisting tool 10 that is shown in FIGS. 1 and 2, the guide unit 14 has the form of the hole (14A) which is disposed in the guide unit 14. In contrast, as shown in FIG. 7, a guide unit 48 that is disposed in a guide body 46 of a puncture assisting tool 10a according to the modification example is formed into a concave shape extending in an arc shape to be in contact only with the outer side of the outer needle 32 of the puncture tool 30. A curvature of the guide unit 48 is approximately the same as the curvature of the outer needle 32. Even with the concave-shaped guide unit 48 that is in contact only with the outer side of the outer needle 32, the outer needle 32 can be guided to be moved while drawing the arc trajectory. Accordingly, the force added to the puncture tool 30 is appropriately transmitted in the moving direction of the puncture tool 30, and the insertion of the puncture tool 30 into the patient can be easily and accurately performed.

First Embodiment of Puncture Tool Assembly

Figure 8:
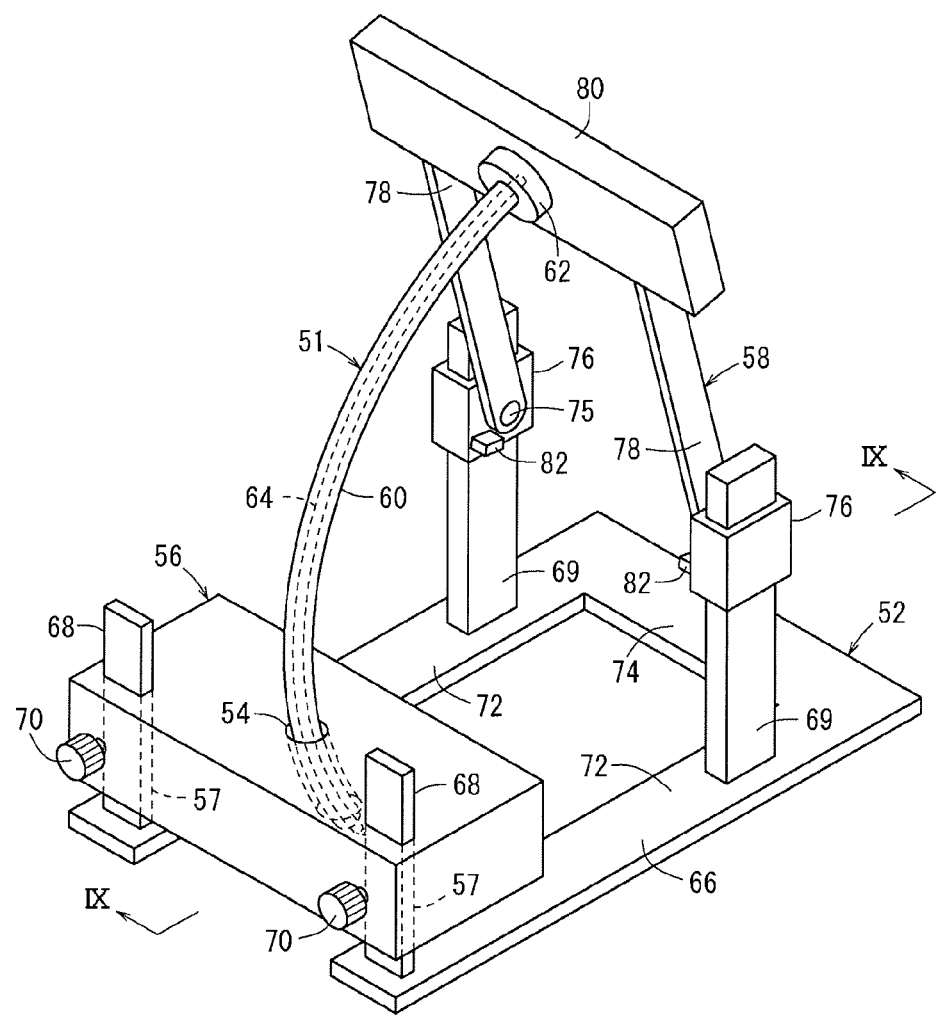
FIG. 8 is an overall perspective view of a puncture tool assembly according to a first embodiment of the present invention.
Figure 9A:
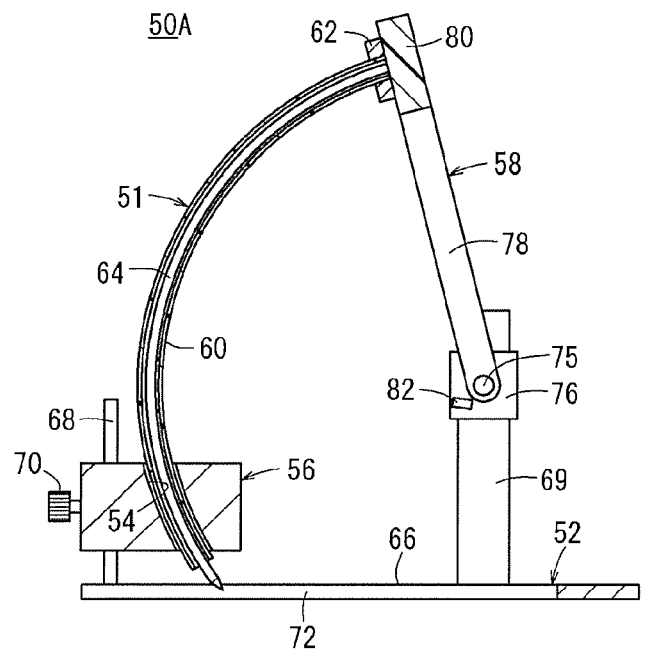
FIG. 9A is a longitudinal cross-sectional view taken along line IX-IX of FIG. 8.
Figure 9B:
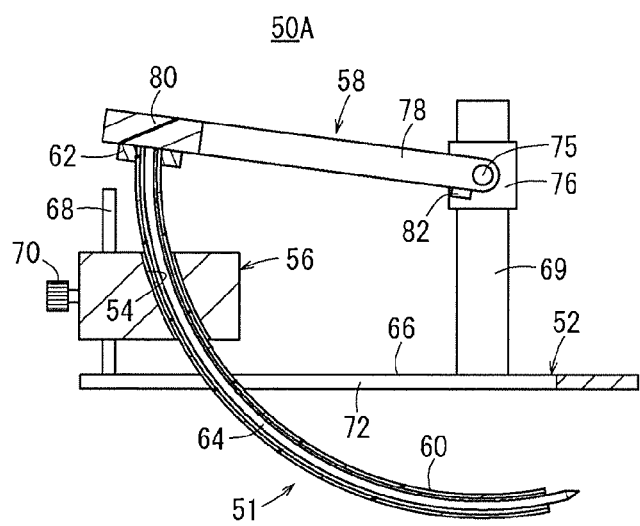
FIG. 9B is a longitudinal cross-sectional view showing a state where the connection device is rotated to a rotation regulation position.

Next, a puncture tool assembly 50A according to the first embodiment of the present invention will be described referring to FIGS. 8 to 9B. FIG. 8 is an overall perspective view of the puncture tool assembly 50A, and FIG. 9A is a longitudinal cross-sectional view taken along line IX-IX of FIG. 8. The puncture tool assembly 50A includes a puncture tool 51 that is inserted into the living body, a base section 52 that is brought into contact with the skin of the patient, a guide unit 54 whose position with respect to the base section 52 can be fixed, a guide body 56 where the guide unit 54 is formed, and guide rails 68 that connect the base section 52 with the guide body 56.

The puncture tool 51 has an outer needle 60 that is curved into an arc shape, a hub 62 that is fixed to a proximal end of the outer needle 60, and an inner needle 64 that can be inserted into the outer needle 60 and is curved into an arc shape. The outer needle 60, the hub 62, and the inner needle 64 of the puncture tool 51 have the same configuration as the outer needle 32, the hub 34, and the inner needle 36 shown in FIG. 3.

The base section 52 has a plate-shaped contact plate 66, a pair of the guide rails 68 that project upward from one end side of the contact plate 66, and a pair of guide pillars 69 that project upward from the other end side of the contact plate 66. In this embodiment, the contact plate 66 has extension sections 72 that extend apart from and in parallel with each other, and an intermediate section 74 that connects the extension sections 72 with each other on the other end side of the contact plate 66. The contact plate 66 is not limited to the flat plate shape, but may be configured into a curved shape or a wave shape to match the shape of the skin when put on the skin of the patient. A plurality of small projections may be disposed on a lower surface of the contact plate 66, and the contact plate 66 and the skin may be configured to be in point contact with each other at a plurality of positions so that the contact plate 66 is stabilized when the contact plate 66 is put on the skin of the patient. In addition, a gel-like sheet may be attached to a contact site between the contact plate 66 and the skin so as to be changed and attached according to the shape of the body and fit the shape of the body.

The guide rails 68 support the guide body 56 such that a position thereof can be changed upward and downward and, in this embodiment, project in parallel with each other and upward from the one end side of the contact plate 66.

The guide unit 54 has a curvature that is approximately the same as curvatures of the arc shapes of the outer needle 60 and the inner needle 64, and is in contact with an outer side of the arc shape of the outer needle 60 such that the outer needle 60 is guided in such a manner as to be moved while drawing an arc trajectory. In this embodiment, the guide unit 54 is configured to have a hole that has an inner diameter which allows the outer needle 60 to be inserted. An inner diameter of the guide unit 54 may be slightly larger than an outer diameter of the outer needle 60 or be approximately the same as the outer diameter of the outer needle 60 such that the outer needle 60 is moved while drawing an accurate arc trajectory. Because the guide unit 54 is disposed in this manner, the puncture tool 51 can be moved such that the arc trajectory of the same center of curvature and radius of curvature as the outer needle 60 is drawn by moving the puncture tool 51 in a distal end direction while bringing the guide unit 54 and the outer needle 60 into contact with each other when the puncture tool 51 is inserted into the patient, and the insertion of the puncture tool 51 into the patient can be easily performed. Also, when the outer needle 60 is withdrawn after the insertion of the puncture tool 51 into the patient, the withdrawal movement of the outer needle 60 can be smoothly performed because the guide unit 54 guides the outer needle 60 such that the arc trajectory is drawn. The concave-shaped guide unit 48 that extends in an arc shape as shown in FIG. 7 may be adopted instead of the guide unit 54, which has the form of the hole.

The guide unit 54 is formed in the guide body 56. Specifically, the guide body 56 is a block-shaped member, and both ends of the guide unit 54 are open to an upper surface and a lower surface thereof. Two slide holes 57 are formed in an up-down direction through the guide body 56. The guide rails 68 are inserted into the slide holes 57. Accordingly, a height of the guide body 56 can be adjusted along the guide rails 68.

A fixing screw 70, which is similar to the fixing screw 24 shown in FIG. 2, is disposed in the puncture tool assembly 50A so as to fix the position of the guide body 56 with respect to the guide rail 68. Accordingly, the guide body 56 can be moved with respect to the guide rail 68 when the fixing screw 70 is loosened, and the movement of the guide body 56 with respect to the guide rail 68 is prevented and the height of the guide body 56 can be fixed to the position when the fixing screw 70 is fastened. In this manner, the fixing screw 70 functions as means for steplessly adjusting the height of the guide body 56.

Steplessly adjusting the height of the guide body 56 with respect to the base section 52 is not limited to the use of the fixing screw 70, but may be accomplished by other physical engagement means. In addition, the means for adjusting the height of the guide body 56 with respect to the base section 52 is not limited to the means for the stepless adjustment, but may be those that can adjust the height with a small pitch.

The guide pillars 69 are respectively disposed at a pair of the extension sections 72, and oppose each other in parallel with each other on the other end side of the contact plate 66. Sliders 76 are disposed in the respective guide pillars 69 such that the slider 76 can be moved in an up-down direction along the guide pillar 69 and can be fixed to any position. Although not shown in FIG. 8, means similar to the above-described means for fixing the position of the guide body 56 with respect to the guide rail 68 can be applied as means for fixing the position of the slider 76 with respect to the guide pillar 69.

Connection device 58 has one end side fixed to the puncture tool 51, and is rotatably supported by the base section 52 by using a center of curvature of an arc shape of the puncture tool 51 as a rotation fulcrum. In this embodiment, the connection device 58 has a pair of arm sections 78 that are rotatably connected to the base section 52 (specifically, the slider 76) via a shaft section 75 and extend in parallel with each other, and a connection section 80 that connects the pair of arm sections 78 with each other on the opposite side from the rotation fulcrum (shaft section 75). A proximal end of the inner needle 64 is fixed to a central portion of the connection section 80. In this embodiment, the connection section 80 is shaped to linearly extend in a direction orthogonal to the arm sections 78 but, instead, may be shaped such that distal ends of the arm sections 78 are curved and connected with each other and configured such that the entire connection device 58 has a U shape or a V shape.

In FIG. 8, the arm sections 78 are rotatably connected to inner sides of a pair of the sliders 76 but, instead of this configuration, the arm sections 78 may be rotatably connected to outer sides of the pair of sliders 76.

Further, a stopper 82 that regulates an insertion length of the puncture tool 51 is disposed in the puncture tool assembly 50A. In this embodiment, the stopper 82 is disposed to project from the inner side surfaces of the pair of sliders 76. As shown in FIG. 9B, when the connection device 58 is rotated and the arm section 78 abuts against the stopper 82, further rotation of the connection device 58 is prevented. Accordingly, the insertion length of the puncture tool 51 fixed to the connection device 58 is appropriately limited with respect to the living body.

A stopper having a different configuration may be, for example, a stopper that moves upward and downward along the guide pillar 69. In this case, a position of the stopper having the different configuration may be adjusted according to an upward and downward position adjustment of the slider 76 to regulate the insertion length of the puncture tool 51.

Each member constituting the puncture assisting tool 50A is not particularly limited if the member is a hard material that has a moderate strength not to be damaged or substantially deformed when the puncture tool 51 is guided such that the puncture tool 51 is punctured into the living body. Examples thereof include a metal such as stainless steel, an aluminum alloy, and a copper-based alloy, or a hard resin such as polyvinyl chloride and polyethylene.

According to the puncture tool assembly 50A of this embodiment that has the above-described configuration, the outer needle 60 of the puncture tool 51 is inserted while being in contact with the guide unit 54 when the puncture tool 51 is inserted into the patient, and thus the direction of the force added from a proximal end side of the puncture tool 51 is corrected to the needle tip direction. In this manner, the force added to the puncture tool 51 is appropriately transmitted in a moving direction of the needle (outer needle 60 and the inner needle 64), and thus the insertion of the needle into the patient can be easily and accurately performed.

In the case of this embodiment, the puncture tool 51 rotates about the rotation fulcrum (shaft section 75) of the connection device 58, and a position of the rotation fulcrum can be fixed. Accordingly, when the puncture tool 51 is inserted into the living body, the puncture tool 51 can be rotated about the fixed rotation fulcrum, and the insertion can be performed more accurately and smoothly.

In the case of this embodiment, the connection device 58 to which the puncture tool 51 is fixed is supported by the pair of guide pillars 69 via the slider 76, and thus the puncture tool 51 can be stably rotated to be moved while the accurate arc trajectory is drawn when the puncture tool 51 is inserted into the living body. Accordingly, the insertion operation can be performed more accurately and smoothly.

In the case of this embodiment, the height of the guide body 56 and a height of the rotation fulcrum of the connection device 58 are variable. Accordingly, an insertion depth of the puncture tool 51 can be easily adjusted according to the shape of the body of the patient, and there is no need to prepare a puncture tool assembly 50 that is set individually for each insertion depth.

In the case of this embodiment, the stopper 82 that regulates the insertion length of the puncture tool 51 is provided, and thus the insertion length of the puncture tool 51 can be appropriately regulated and the puncture tool 51 can be inserted at a desired insertion length into the living body.

In the case of this embodiment, the connection device 58 has the pair of arm sections 78 that extend in parallel with each other, and the connection section 80 that connects the pair of arm sections 78 with each other on the opposite side from the rotation fulcrum, and thus a gap having a predetermined size is formed between the pair of arm sections 78. In addition, on the contact plate 66 of the base section 52, a gap having a predetermined size is formed between the pair of extension sections 72. Accordingly, in a plan view of the puncture tool assembly 50, the outer needle 60 and the inner needle 64 of the puncture tool 51 are positioned between the pair of arm sections 78 and the pair of extension sections 72 with regard to a separation direction of the guide pillars 69.

According to this configuration, the arm section 78 and the extension section 72 are not present between an X-ray irradiation source and the outer needle 60 and the inner needle 64 of the puncture tool 51 when the insertion length (insertion depth) of the puncture tool 51 is determined by emitting the X-ray from above the puncture tool assembly 50A. Accordingly, the gaps disposed between the arm sections 78 and between the extension sections 72 are spaces that pass the X-ray as it is, and thus the X-ray fluoroscopic image can be appropriately obtained without the X-ray being attenuated by a structure of the puncture tool assembly 50.

Second Embodiment of Puncture Tool Assembly 50

Figure 10:
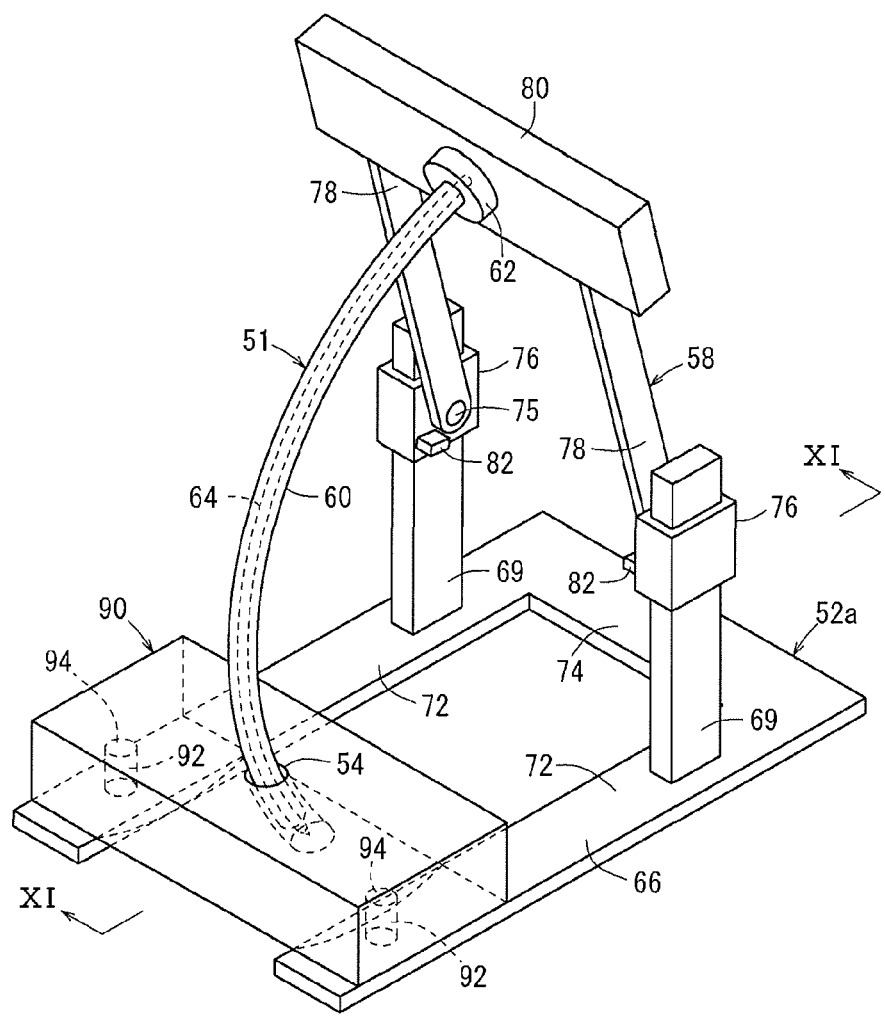
FIG. 10 is an overall perspective view of a puncture tool assembly according to a second embodiment of the present invention.
Figure 11:
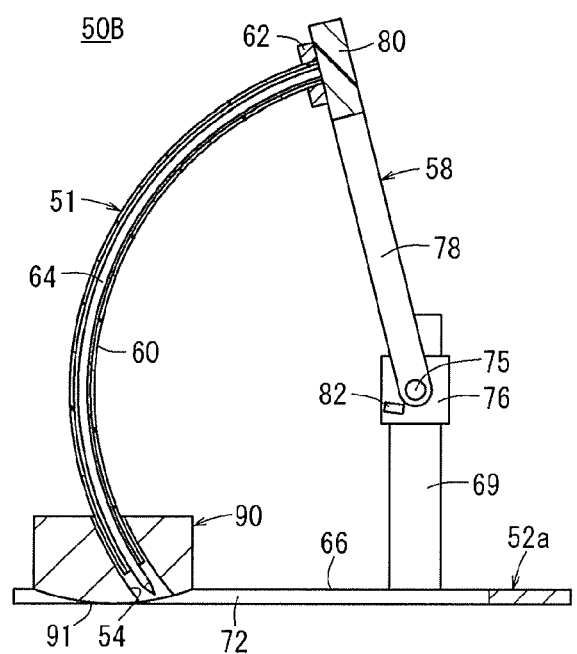
FIG. 11 is a longitudinal cross-sectional view taken along line XI-XI of FIG. 10.

Next, a puncture tool assembly 50B according to the second embodiment of the present invention will be described referring to FIGS. 10 and 11. FIG. 10 is an overall perspective view of the puncture tool assembly 50B, and FIG. 11 is a longitudinal cross-sectional view taken along line XI-XI of FIG. 10. In the puncture tool assembly 50B according to the second embodiment, the same reference numerals are attached to elements achieving the same or similar functions or effects as in the puncture tool assembly 50A according to the first embodiment, and detailed description will be omitted.

The second embodiment includes a pressing member 90, instead of the guide rail 68 and the guide body 56 of the first embodiment, which can be attached to the contact plate 66. Accordingly, unlike in the base section 52 of the first embodiment, the guide rail 68 is not disposed in a base section 52a of the second embodiment.

The pressing member 90 is in contact with the skin of the patient to suppress the deformation of the skin and a repulsive force from the skin at an insertion point, and the guide unit 54 is disposed in an arc shape. Instead of the guide unit 54 that has the form of the hole, the concave-shaped guide unit 48 that extends in an arc shape as shown in FIG. 7 may be adopted.

The pressing member 90 is removable from the contact plate 66 of the base section 52a. In this embodiment, a positioning pin 92 is disposed on the contact plate 66, a positioning hole 94 is disposed in the pressing member 90, and the positioning pin 92 and the positioning hole 94 are fitted to each other such that the pressing member 90 is attached in a state of being positioned with respect to the contact plate 66. The positioning hole 94 may be disposed on the contact plate 66 and the positioning pin 92 may be disposed in the pressing member 90. Means for removably mounting the pressing member 90 on the contact plate 66 is not limited to the configurations of the positioning pin 92 and the positioning hole 94, but may be other physical engagement means or a fixing member (clip or the like) that is configured independently of the pressing member 90 and the contact plate 66.

In the case of this embodiment, a height of the pressing member 90 cannot be adjusted with respect to the base section 52, and thus a plurality of types of the pressing members 90 in which the guide unit 54 has different angles according to the insertion depth (insertion length) of the puncture tool 51 with respect to the patient are prepared. Accordingly, when the insertion depth of the puncture tool 51 is adjusted, the slider 76 is moved to adjust the height of the rotation fulcrum, and the pressing member 90 in which the guide unit 54 with an angle corresponding to the height of the rotation fulcrum is disposed is selected to be attached to the contact plate 66 of the base section 52.

As shown in FIG. 11, a bloated part 91 whose portion in contact with the skin is formed to be round is disposed in a lower portion of the pressing member 90. A lower end of the guide unit 54 is formed to face a skin contact surface of the pressing member 90.

According to the puncture tool assembly 50B of this embodiment, the pressing member 90 presses the skin of the patient in a vicinity of the insertion point when the puncture tool 51 is inserted into the patient. Accordingly, the deformation of the skin and the repulsive force from the skin can be suppressed, and the insertion of the puncture tool 51 into the patient can be more easily performed.

In the case of this embodiment, the portion (lower portion) of the pressing member 90 that is in contact with the skin is formed to be round, and thus the skin contact surface of the pressing member 90 can have a large area and an effect of the suppression of the deformation of and the repulsive force from the skin can be increased.

As a matter of course, with each of the components of the second embodiment which are common to each of those of the first embodiment, the same or similar operation and effect as achieved in the first embodiment can be achieved.
Third Embodiment of Puncture Tool Assembly 50

Figure 12:
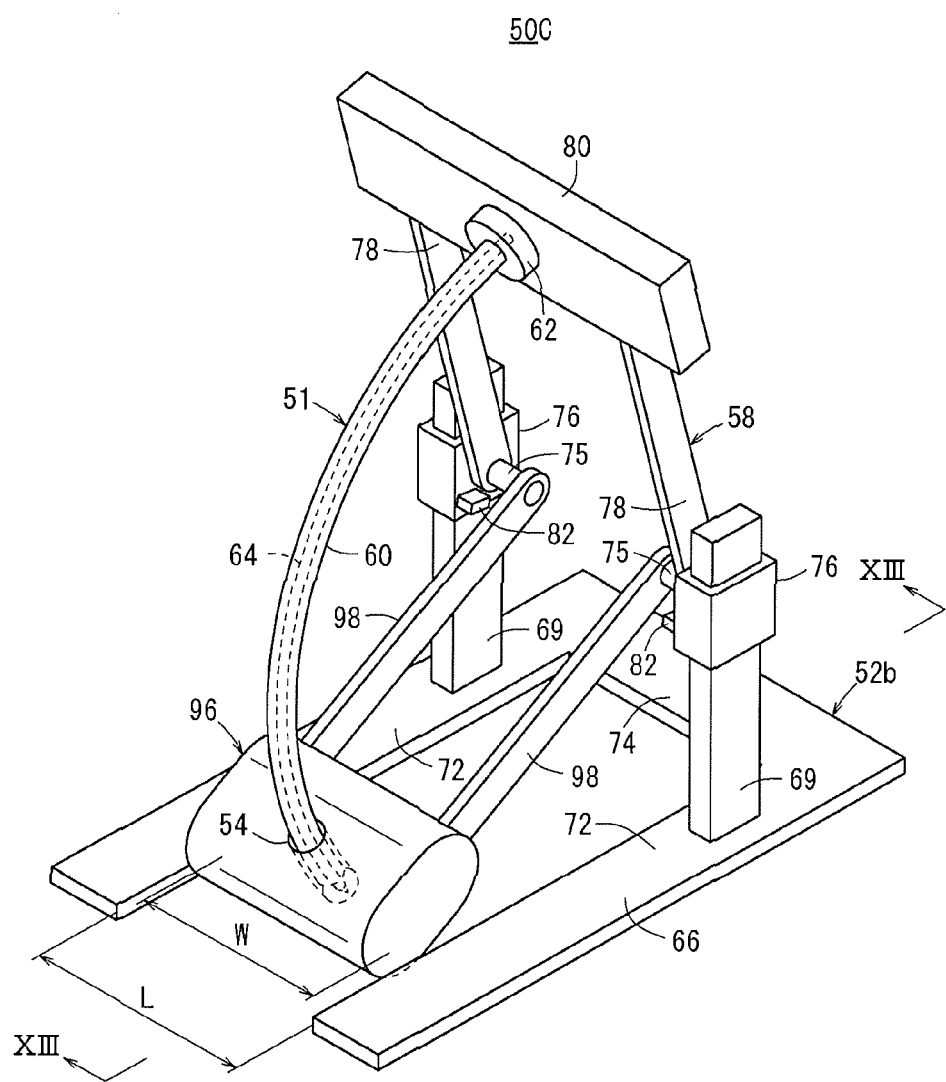
FIG. 12 is an overall perspective view of a puncture tool assembly according to a third embodiment of the present invention.
Figure 13:
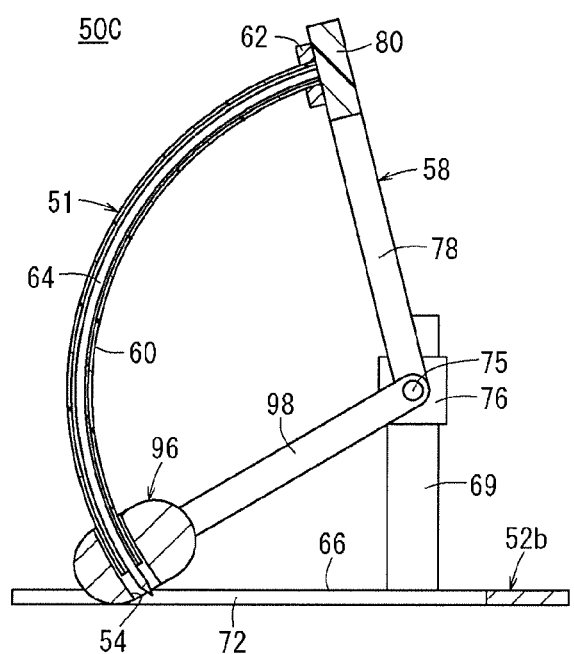
FIG. 13 is a longitudinal cross-sectional view taken along line XIII-XIII of FIG. 12.

Next, a puncture tool assembly 50C according to the third embodiment of the present invention will be described referring to FIGS. 12 and 13. FIG. 12 is an overall perspective view of the puncture tool assembly 50C, and FIG. 13 is a longitudinal cross-sectional view taken along line XIII-XIII of FIG. 12. In the puncture tool assembly 50C according to the third embodiment, the same reference numerals are attached to elements achieving the same or similar functions or effects as in the puncture tool assembly 50A according to the first embodiment, and detailed description will be omitted.

The third embodiment includes a pressing member 96 and a pair of connection arms 98 instead of the guide rail 68 and the guide body 56 of the first embodiment. Accordingly, unlike in the base section 52 of the first embodiment, the guide rail 68 is not disposed in a base section 52b of the third embodiment.

The pressing member 96 is in contact with the skin of the patient to suppress the deformation of the skin and the repulsive force from the skin at the insertion point, and the arc-shaped guide unit 54 is disposed in the pressing member 96. Instead of the guide unit 54 that has the form of the hole, the concave-shaped guide unit 48 that extends in an arc shape as shown in FIG. 7 may be adopted.

As shown in FIG. 13, the lower end of the guide unit 54 is formed to face a skin contact surface of the pressing member 96. A portion of the pressing member 96 that is in contact with the skin is formed to be round such that the skin contact surface has a large area. As shown in FIG. 12, a width W of the pressing member 96 is smaller than a gap L between the extension sections 72 of the contact plate 66. Accordingly, in a state where the puncture tool assembly 50 is put on the patient, the pressing member 96 is put between the pair of extension sections 72 and can be in contact with the skin of the patient.

A distal end side of the connection arm 98 is connected to the pressing member 96, and a proximal end side of the connection arm 98 is pivotally connected to the slider 76 via the shaft section 75. The connection arm 98 and the arm section 78 are pivotable about the same shaft center. Accordingly, the pressing member 96 that is fixed to a distal end of the connection arm 98 can be rotated about the rotation fulcrum (shaft section 75) of the connection device 58. The guide unit 54 that is disposed in the pressing member 96 can be rotated with the same center of rotation and turning radius as a center of rotation and turning radius of the puncture tool 51.

According to the puncture tool assembly 50C of this embodiment that has the above-described configuration, the angle of the guide unit 54 based on the rotation fulcrum can be changed according to the height of the rotation fulcrum of the connection device 58. Accordingly, unlike in the puncture tool assembly 50B according to the second embodiment, there is no need to prepare a plurality of the pressing members 96 corresponding to the height of the rotation fulcrum of the connection device 58.

In a plan view of the puncture tool assembly 50C, the outer needle 60 and the inner needle 64 of the puncture tool 51 are positioned between the pair of arm sections 78, the pair of extension sections 72, and between the pair of connection arms 98 with regard to the separation direction of the pair of guide pillars 69. According to this configuration, the arm section 78, the extension section 72, and the connection arm 98 are not present between the X-ray irradiation source and the outer needle 60 and the inner needle 64 of the puncture tool 51 when the insertion length (insertion depth) of the puncture tool 51 is determined by emitting the X-ray from above the puncture tool assembly 50C, and thus the X-ray fluoroscopic image can be appropriately obtained. In other words, the gaps disposed between the arm sections 78, between the extension sections 72, and between the connection arms 98 are spaces that pass the X-ray as it is, and thus the X-ray is not attenuated by the structure of the puncture tool assembly 50C.

Among the members constituting the puncture tool assembly 50C, the outer needle 60 and the pressing member 96 may be separable from the other members. In this case, the configuration may be, for example, as shown in FIGS. 14A and 14B. In FIG. 14A, an engagement pin 100 that projects in a direction orthogonal to an extension direction of the connection arm 98 is disposed at the distal end of the connection arm 98, and the engagement pin 100 is engaged with an engagement hole 102 that is disposed in the pressing member 96. A captive screw 104 is screwed with the pressing member 90, and the engagement pin 100 does not come off the engagement hole 102 because of the captive screw 104.

As shown in FIG. 14B, the engagement pin 100 comes off the engagement hole 102 and the engagement is released when the gap between the connection arms 98 is widened in a state where the captive screw 104 is loosened. Accordingly, the pressing member 90 and the connection arm 98 can be separated from each other.

During the use of the puncture tool assembly 50C, the outer needle 60 is inserted into the living body along the guide unit 54 that is disposed in the pressing member 96, and then the connection device 58 is rotated in a reverse direction so that the inner needle 64 is removed from the outer needle 60. Then, when the spacer 42 (refer to FIG. 6A) is inserted into the outer needle 60, the insertion operation is easier to be performed if the inner needle 64 or the like is not present. If the connection arm 98 is separated from the pressing member 96, only the outer needle 60 (and the hub 62) and the pressing member 96 are left, and the other members can be removed from the patient. Accordingly, during the insertion operation of the spacer 42, the surrounding members pose no inconvenience and the insertion operation can be smoothly performed. The connection arm 98 may be configured to be separable from the base section 52*b* (slider 76).

Also, among the members constituting the puncture tool assemblies 50A and 50B according to the above-described first and second embodiments and a puncture tool assembly 50D according to a fourth embodiment that will be described later, the outer needle 60, the guide body 56, and the pressing members 90 and 110 may be separable from the other members.

As a matter of course, with each of the components of the third embodiment which are common to each of those of the first embodiment, the same or similar operation and effect as achieved in the first embodiment can be achieved.

Fourth Embodiment of Puncture Tool Assembly 50

Figure 15:
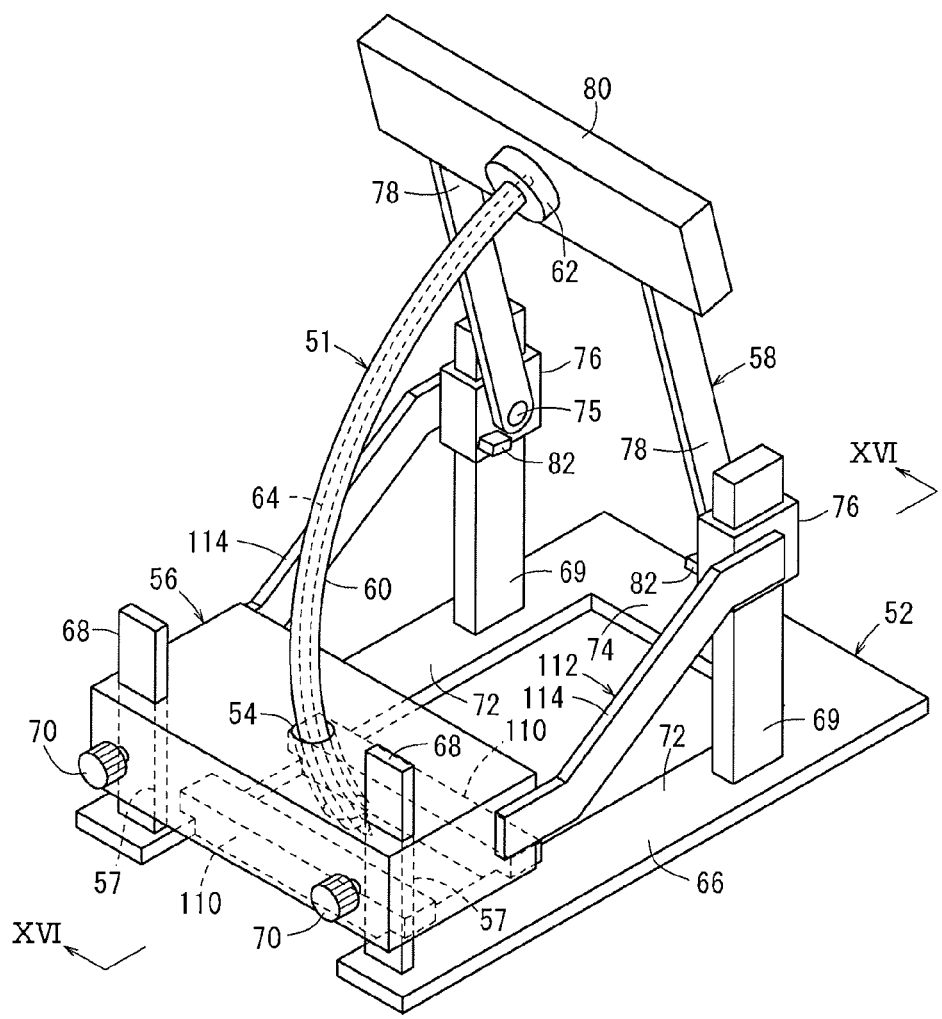
FIG. 15 is an overall perspective view of a puncture tool assembly according to a fourth embodiment of the present invention.
Figure 16:
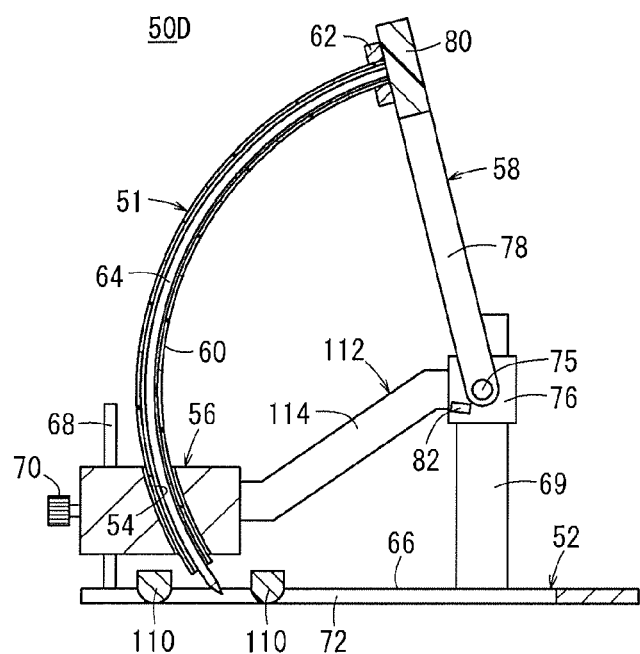
FIG. 16 is a longitudinal cross-sectional view taken along line XVI-XVI of FIG. 15.

Next, the puncture tool assembly 50D according to the fourth embodiment of the present invention will be described referring to FIGS. 15 and 16. FIG. 15 is an overall perspective view of the puncture tool assembly 50D, and FIG. 16 is a longitudinal cross-sectional view taken along line XVI-XVI of FIG. 15. In the puncture tool assembly 50D according to the fourth embodiment, the same reference numerals are attached to elements achieving the same or similar functions or effects as in the puncture tool assembly 50A according to the first embodiment, and detailed description will be omitted.

The puncture tool assembly 50D of the fourth embodiment is the puncture tool assembly 50A of the first embodiment added with the pressing member 110 and linking device 112.

The pressing member 110 is in contact with the skin of the patient in the vicinity of the insertion point of the puncture tool 51 to suppress the deformation of the skin and the repulsive force from the skin at the insertion point, and is fixed to the contact plate 66 below the guide body 56. As shown in FIG. 16, a portion of the pressing member 110 that is in contact with the skin is formed to be round, or a deformable gel-like material may be used in the portion of the pressing member 110 that is in contact with the skin so as to increase a contact force with respect to the skin.

In this embodiment, a pair of the pressing members 110 are disposed at positions having a gap in an extension direction of the extension sections 72, and are bridged between the left and right extension sections 72. The inner needle 64 and the outer needle 60 of the puncture tool 51 can be inserted into the living body through the gap between the pair of pressing members 110.

The linking device 112 links the height of the rotation fulcrum of the connection device 58 with the height of the guide body 56. Specifically, the linking device 112 has a pair of connection bodies 114. One end of each of the connection bodies 114 is fixed to the guide body 56, and the other end of each of the connection bodies 114 is fixed to each of the pair of sliders 76. According to this configuration, the height of the guide body 56 can be changed, linked to the rotation fulcrum of the connection device 58, by an operation of the linking device 112 resulting from the adjustment of the height of the rotation fulcrum of the connection device 58 by changing the position of the slider 76.

According to the puncture tool assembly 50D of this embodiment that has the above-described configuration, the pressing member 110 presses the skin of the patient in the vicinity of the insertion point when the puncture tool 51 is inserted into the patient. Accordingly, the deformation of the skin and the repulsive force from the skin can be suppressed, and the insertion of the puncture tool 51 into the patient can be further easily performed.

In addition, according to the configuration of this embodiment, the linking device 112 is provided, and thus the height of the rotation fulcrum of the connection device 58 is linked with the height of the guide body 56. Accordingly, there is no need for individually adjusting the heights of the rotation fulcrum of the connection device 58 and the guide body 56, and convenience of use is increased.

As a matter of course, with each of the components of the fourth embodiment which are common to each of those of the first embodiment, the same or similar operation and effect as achieved in the first embodiment can be achieved.

Several embodiments of the present invention have been described above, but the present invention is not limited to the embodiments and various modifications are possible without departing from the scope of the present invention.

What is claimed is:

1. A puncture assisting tool for assisting in a puncturing operation by a puncture tool that is used to insert and place a spacer between bones and includes a hollow, arc-shaped outer needle and an arc-shaped needle, the puncture assisting tool comprising:
 a base section configured to be in contact with a skin of a patient; and
 a guide unit configured to be fixed with respect to the base section,
 wherein the guide unit has a curvature that is approximately the same as a curvature of an arc shape of the puncture tool, and
 wherein the guide unit comprises a surface configured to slidably contact an outer arc-shaped surface of the outer needle while the puncture tool is being inserted into the patient so as to guide the puncture tool in an arc trajectory.

2. The puncture assisting tool according to claim 1, further comprising:
 a guide body configured such that a height of the guide body is variable with respect to the base section,
 wherein the guide unit is disposed in the guide body.

3. The puncture assisting tool according to claim 2, wherein the guide body is configured such that the guide body is steplessly adjustable in height with respect to the base section.

4. The puncture assisting tool according to claim 1, wherein the guide unit is a hole that has approximately the same diameter as an outer diameter of the puncture tool.

5. The puncture assisting tool according to claim 1, wherein the guide unit is formed in a concave shape extending in an arc shape.

6. The puncture assisting tool according to claim 1, wherein the guide unit is configured to redirect a force applied from a proximal end side of the puncture tool to a direction of a tip of the arc-shaped needle of the puncture tool.

7. A puncture tool assembly comprising:
 a puncture tool comprising:
  a hollow, arc-shaped outer needle; and
  an arc-shaped inner needle that has the same curvature as the outer needle and that is insertable into the outer needle;
 a base section configured to be in contact with a skin of a patient;
 a guide unit configured to be fixed with respect to the base section; and a connection device to which the inner needle is fixed, the connection device being rotatably supported by the base section and configured such that a rotation fulcrum of the connection device is located at a center of curvature of the arc shape of the inner needle, wherein the guide unit has a curvature that is approximately the same as a curvature of the arc shape of the outer needle, and wherein the guide unit comprises a surface configured to slidably contact an outer arc-shaped surface of the outer needle while the puncture tool is being inserted into the patient so as to guide the puncture tool in an arc trajectory.

8. The puncture tool assembly according to claim 7, further comprising:
a guide body configured such that a height of the guide body is variable with respect to the base section,
wherein the guide unit is disposed in the guide body, and
wherein a height of the rotation fulcrum of the connection device is variable with respect to the base section.

9. The puncture tool assembly according to claim 8, wherein the outer needle and the guide body are separable from a remainder of the puncture tool assembly.

10. The puncture tool assembly according to claim 7, further comprising a pressing member configured to be placed in contact with a skin of a patient and configured to suppress a deformation of the skin and a repulsive force from the skin at an insertion point, wherein the guide unit is disposed in the pressing member.

11. The puncture tool assembly according to claim 10, wherein a height of the rotation fulcrum of the connection device is variable with respect to the base section, and the guide unit is rotatable with the same center of rotation and turning radius as a center of rotation and turning radius of the puncture tool.

12. The puncture tool assembly according to claim 10, wherein the outer needle and the pressing member are separable from a remainder of the puncture tool assembly.

13. The puncture tool assembly according to claim 10, wherein a portion of the pressing member that is in contact with the skin is rounded.

14. The puncture tool assembly according to claim 7, further comprising:
a pressing member configured to be placed in contact with a skin of a patient and configured to suppress a deformation of the skin and a repulsive force from the skin at an insertion point; and
a guide body configured such that the height of the guide body is variable with respect to the base section,
wherein the guide unit is disposed in the guide body, and
wherein a height of the rotation fulcrum of the connection device is variable with respect to the base section.

15. The puncture tool assembly according to claim 14, further comprising a linking device that links the rotation fulcrum of the connection device with the guide body such that a height of the rotation fulcrum is adjustable together with a height of the guide body.

16. The puncture tool assembly according to claim 14, wherein a portion of the pressing member that is in contact with the skin is rounded.

17. The puncture tool assembly according to claim 7, further comprising a stopper configured to regulate an insertion length of the puncture tool.

18. The puncture tool assembly according to claim 7, wherein the guide unit is formed into a concave shape extending in an arc shape.

19. The puncture tool assembly according to claim 7, wherein the guide unit is a hole that has approximately the same diameter as an outer diameter of the outer needle.

20. The puncture tool assembly according to claim 7, wherein the connection device includes a plurality of arm sections that are rotatably connected to the base section and extend in parallel with each other, and a connection section that connects the plurality of arm sections with each other.

* * * * *